United States Patent
Anzai et al.

(10) Patent No.: US 12,195,708 B2
(45) Date of Patent: Jan. 14, 2025

(54) CELL CULTURE SUBSTRATE

(71) Applicant: TERUMO KABUSHIKI KAISHA, Tokyo (JP)

(72) Inventors: Takao Anzai, Kanagawa (JP); Ichiro Hirahara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 804 days.

(21) Appl. No.: 17/415,456

(22) PCT Filed: Dec. 18, 2019

(86) PCT No.: PCT/JP2019/049581
§ 371 (c)(1),
(2) Date: Jun. 17, 2021

(87) PCT Pub. No.: WO2020/130032
PCT Pub. Date: Jun. 25, 2020

(65) Prior Publication Data
US 2022/0073853 A1    Mar. 10, 2022

(30) Foreign Application Priority Data
Dec. 20, 2018 (JP) ................................. 2018-238596

(51) Int. Cl.
C12M 1/00 (2006.01)
C08F 220/28 (2006.01)
C12N 5/00 (2006.01)

(52) U.S. Cl.
CPC ......... *C12M 23/20* (2013.01); *C08F 220/281* (2020.02); *C12N 5/0068* (2013.01); *C12N 2533/30* (2013.01)

(58) Field of Classification Search
None
See application file for complete search history.

(56) References Cited

U.S. PATENT DOCUMENTS

| | | | | |
|---|---|---|---|---|
| 8,354,274 B2 * | 1/2013 | Fadeev | ............... | C12N 5/0068 435/174 |
| 2009/0191634 A1 * | 7/2009 | Martin | ................ | C08J 7/043 526/260 |

FOREIGN PATENT DOCUMENTS

| | | | |
|---|---|---|---|
| EP | 2598518 A1 * | 6/2013 | ............ C07K 14/78 |
| JP | 2010-523118 | 7/2010 | |
| JP | 2018012811 A * | 1/2018 | |
| KR | 10-2018-0075126 | 7/2018 | |
| WO | 2016159153 A1 | 6/2016 | |
| WO | 2018008985 A2 | 11/2018 | |

OTHER PUBLICATIONS

Lerman et al. The Evolution of Polystyrene as a Cell Culture Material. Tissue Engineering Part B (2018), 24(5), 359-372. (Year: 2018).*
Official Action with Machine Translation for Japan Patent Application No. 2021-524052, dated Aug. 1, 2023, 5 pages.
Hutcheon et al., "Water absorption and surface properties of novel poly(ethylmethacrylate) polymer systems for use in bone and cartilage repair," Biomaterials, vol. 22, 2001, pp. 667-676.
Patel et al., "A defined synthetic substrate for serum-free culture of human stem cell derived cardiomyocytes with improved functional maturity identified using combinatorial materials microarrays," Biomaterials, vol. 61, May 15, 2015, pp. 257-265.
Sato et al., "Blood-compatible poly(2-methoxyethyl acrylate) for the adhesion and proliferation of endothelial and smooth muscle cells," Colloids and Surfaces B: Biointerfaces, vol. 145, Sep. 1, 2016, pp. 586-596.
International Search Report and Written Opinion for International (PCT) Patent Application No. PCT/JP2019/049581, dated Apr. 9, 2020, 8 pages.

* cited by examiner

*Primary Examiner* — Sean C. Barron
(74) *Attorney, Agent, or Firm* — Sheridan Ross P.C.

(57) ABSTRACT

To provide a means capable of providing excellent cell adhesion to a polymer substrate (particularly, a hydrophilic polymer substrate) as compared to the case of performing a surface treatment with polytetrahydrofurfuryl acrylate (PTHFA).
Provided is a cell culture substrate comprising a coating layer on at least one side of a polymer substrate, wherein the coating layer includes a copolymer having more than 40% by mole and less than 100% by mole of a structural unit derived from furfuryl (meth)acrylate represented by Formula and more than 0% by mole and less than 60% by mole of a structural unit derived from ethylenically unsaturated monomer having a carboxylic group (the total of the structural unit and the structural unit is 100% by mole).

7 Claims, 1 Drawing Sheet

CELL CULTURE SUBSTRATE

CROSS REFERENCE TO RELATED APPLICATIONS

The present disclosure is a National Stage Entry from PCT Application No. PCT/JP2019/049581 filed on Dec. 18, 2019, which claims priority to Japanese Patent Application No. 2018-238596, filed on Dec. 20, 2018, which are hereby incorporated herein by reference, in their entireties, for all that they teach and for all purposes.

TECHNICAL FIELD

The present invention relates to a cell culture substrate excellent in cell adhesion, and a bioreactor and a method for culturing a cell using the cell culture substrate.

BACKGROUND

In recent years, a cell culture technology has been used in the development of regenerative medicine or drug discovery. In particular, attention has been paid to use of stem cells, and technology for repairing and replacing damaged or defective tissues has been actively studied by using stem cells expanded from donor cells. Most of cells of animals including humans are adherent (scaffold-dependent) cells which cannot survive in a floating state and survive in a state of being adhered to something. For this reason, various developments of functional culture substrates for culturing adherent (scaffold-dependent) cells at high density to obtain cultured tissues similar to living tissues have been conducted.

As a cell culture substrate, conventionally, plastic or glass vessels have been used, and it has been reported that a plasma treatment or the like is performed to surfaces of these cell vessels. A substrate subjected to the treatment has excellent adhesion to cells, and can be used to grow cells and maintain their function.

Meanwhile, regarding a structure of the cell culture substrate (cell culture vessel), in addition to a conventional flat dish (plate) structure, various structures, such as a structure in which a porous body is inserted as a culture scaffold in a bag, a hollow fiber structure, a sponge structure, a flocculent (glass wool) structure, and a structure in which a plurality of dishes are laminated, have been developed. It is difficult or impossible to perform plasma treatment with respect to culture vessels having such diversified or complicated structures.

In a cell culture technique using a hollow fiber type bioreactor, an improvement in cell adhesion to a hollow fiber membrane by methods other than the plasma treatment has been under review. For example, Patent Literature 1 discloses that cell adhesion to a hollow fiber membrane is improved by subjecting the hollow fiber membrane to a surface treatment with a cell adhesion factor such as platelet lysate, plasma, or fibronectin; however, the cell adhesion factor is expensive.

Meanwhile, disclosed is coating using a polymer promoting cell adhesion. For example, Non Patent Literature 1 discloses that cell adhesion to a cell culture substrate made of polystyrene is improved by subjecting the cell culture substrate to a surface treatment using a homopolymer of tetrahydrofurfuryl acrylate (PTHFA; polytetrahydrofurfuryl acrylate).

CITATION LIST

Patent Literature

[PTL 1]
Patent Literature 1: JP 2010-523118 A

Non Patent Literature

[NPL 1]
Non Patent Literature 1: Colloids and Surfaces B: Biointerfaces 145 (2016) 586-596.

SUMMARY OF THE INVENTION

The hollow fiber membrane used in the bioreactor is typically subjected to a hydrophilization treatment for performing culture medium replacement. In this regard, the present inventors have studied whether cell adhesion is improved by subjecting a hydrophilic polymer substrate to a surface treatment using PTHFA described in Non Patent Literature 1. As a result, it has been found that although cell adhesion is improved, there is a room for further improvement. Therefore, regarding the hydrophilic cell culture substrate like a hollow fiber membrane for a bioreactor, a further improvement in cell adhesion is required.

The present invention is made in view of the above-described circumstances, and an object thereof is to provide a means capable of providing excellent cell adhesion to a polymer substrate (particularly, a hydrophilic polymer substrate) as compared to the case of performing a surface treatment using polytetrahydrofurfuryl acrylate (PTHFA).

The present inventors have conducted intensive studies to solve the above-described problems. As a result, the present inventors have found that the above-described problems can be solved by coating a surface of a cell culture substrate (polymer substrate) using a copolymer containing a structural unit derived from furfuryl (meth)acrylate having a specific structure and a structural unit derived from an ethylenically unsaturated monomer having a carboxylic group, at a specific composition (molar ratio). The present invention has been completed on the basis of the above finding.

That is, the various objects can be achieved by a cell culture substrate (substrate for cell culture) comprising a coating layer on at least one side of a polymer substrate, wherein the coating layer contains a copolymer comprising more than 40% by mole and less than 100% by mole of a structural unit (1) derived from furfuryl (meth)acrylate represented by the following Formula (1) and more than 0% by mole and less than 60% by mole of a structural unit (2) derived from ethylenically unsaturated monomer having a carboxylic group (the total of the structural unit (1) and the structural unit (2) is 100% by mole).

[Chemical Formula 1]

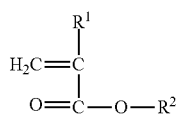

Formula (1)

wherein, $R^1$ represents a hydrogen atom or a methyl group and $R^2$ represents a group represented by the following Formula (1-1) or the following Formula (1-2):

[Chemical Formula 2]

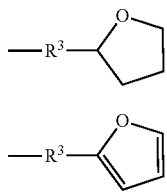

wherein, $R^3$ represents an alkylene group having 1 to 3 carbon atoms.

DETAILED DESCRIPTION

Figure 1:
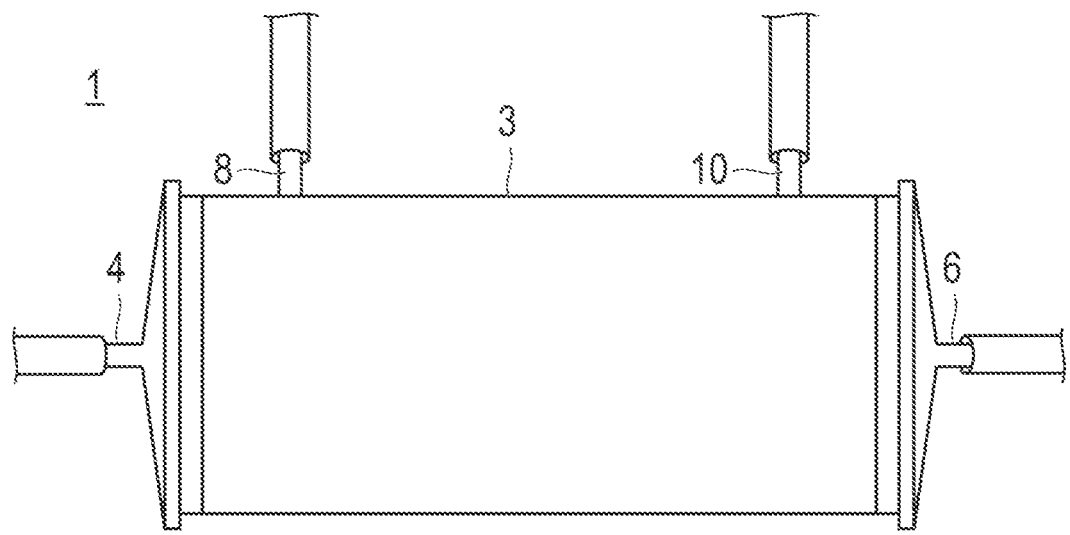
FIG. 1 is a partial side view illustrating an embodiment of a bioreactor (hollow fiber type bioreactor) of the present invention.

A cell culture substrate of the present invention has a coating layer on at least one side of a polymer substrate, wherein the coating layer includes a copolymer comprising more than 40% by mole and less than 100% by mole of a structural unit (1) derived from furfuryl (meth)acrylate represented by the following Formula (1) and more than 0% by mole and less than 60% by mole of a structural unit (2) derived from ethylenically unsaturated monomer having a carboxylic group (the total of the structural unit (1) and the structural unit (2) is 100% by mole).

[Chemical Formula 3]

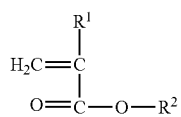

wherein, $R^1$ represents a hydrogen atom or a methyl group and $R^2$ represents a group represented by the following Formula (1-1) or the following Formula (1-2):

[Chemical Formula 4]

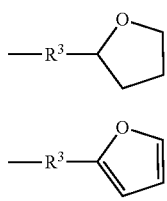

wherein, $R^3$ represents an alkylene group having 1 to 3 carbon atoms.

According to the present invention, it is possible to provide excellent cell adhesion to a polymer substrate (particularly, a hydrophilic polymer substrate) as compared to the case of performing a surface treatment using polytetrahydrofurfuryl acrylate (PTHFA).

In the present description, the furfuryl (meth)acrylate represented by the above Formula (1) is also simply referred to as the "furfuryl (meth)acrylate" and the structural unit derived from furfuryl (meth)acrylate represented by the above Formula (1) is also simply referred to as the "structural unit (1)." Further, the ethylenically unsaturated monomer having a carboxylic group is also simply referred to as "ethylenically unsaturated monomer" and the structural unit derived from ethylenically unsaturated monomer having a carboxylic group is also simply referred to as the "structural unit (2)". Furthermore, the copolymer having the structural unit (1) and the structural unit (2) is also simply referred to as the "copolymer" or the "copolymer according to the present invention."

Further, in the present description, the term "(meth)acrylate" includes both acrylate and methacrylate". Similarly, the term "(meth)acrylic acid" includes both acrylic acid and methacrylic acid, and "(meth)acryloyl" includes both acryloyl and methacryloyl.

Further, in the present description, the term "hydrophilic" indicates that a contact angle of a surface of a target object to water is 50° or less, preferably 40° or less. Incidentally, in the present description, as the contact angle, a value measured by a contact angle meter (measurement method; according to JIS R 3257:1999 (sessile drop method)) is adopted.

The cell culture substrate of the present invention is characterized in that a coating layer containing the copolymer is formed on at least one side of the polymer substrate. The coating layer formed using the copolymer has excellent cell adhesion as compared to a coating layer formed using polytetrahydrofurfuryl acrylate (PTHFA). Here, the mechanism for exhibiting the effects by the present invention is presumed to be as follows. Incidentally, the present invention is not limited to the following presumption.

As described above, in the cell culture technique using the hollow fiber type bioreactor, an improvement in cell adhesion to the hollow fiber membrane is required. The hollow fiber membrane used in the bioreactor is typically subjected to a hydrophilization treatment for performing culture medium replacement. On the other hand, Non Patent Literature 1 discloses that cell adhesion to a cell culture substrate made of polystyrene is improved by subjecting the cell culture substrate to a surface treatment using polytetrahydrofurfuryl acrylate (PTHFA). In this regard, the present inventors have studied whether cell adhesion is improved by subjecting a hydrophilic polymer substrate to a surface treatment using PTHFA. As a result, it has been found that although cell adhesion is improved, there is a room for further improvement (Comparative Examples 1 and 3 described later).

In this regard, the present inventors have conducted intensive studies on a polymer capable of providing excellent cell adhesion to a polymer substrate (particularly, a hydrophilic polymer substrate) as compared to PTHFA. As a result, the present inventors have found that the cell adhesion to the polymer substrate is significantly improved by subjecting the polymer substrate to a surface treatment using the copolymer containing the structural unit (1) and the structural unit (2) at a specific ratio, as compared to the case of performing a surface treatment using PTHFA.

When the polymer substrate is subjected to the surface treatment using the copolymer, a coating layer having appropriate hydrophobicity (for example, having a surface with a contact angle to water of about 60 to 70°) is formed on the polymer substrate. When cells are cultured using the polymer substrate having the coating layer, a cell adhesion factor (cell-adhesive protein) contained in the culture medium is favorably adsorbed to the coating layer, and it is presumed that the cells are easily attached therethrough. Further, the carboxylic group contained in the structural unit (2) is considered to trigger activation or induction of signals of extension (proliferation) of cells or adhesion of cells so that extension (proliferation) or adhesion of cells is promoted. It is considered that by those actions, excellent cell adhesion and further cell extension (proliferation) ability can be provided to the polymer substrate.

Meanwhile, the present inventors have surprisingly found that in a case where the content (ratio) of the structural unit (2) in the copolymer is 60% by mole or more, also compared to the case of PTHFA, cell adhesion is degraded (Comparative Example 2 described later). The cause for this is not clear, but it is presumed that in a case where the content (ratio) of the structural unit (2) in the copolymer is 60% by mole or more, adhesion onto the coating layer (coating film) of components other than the cell adhesion factor (the components being components not having cell adhesion or having low cell adhesion; for example, albumin contained in the culture medium, and the like) becomes more dominant than that of the cell adhesion factor, and the amount of the cell adhesion factor adhered onto the coating layer (coating film) becomes small.

Incidentally, for example, a homopolymer of carboxyalkyl (meth)acrylate such as carboxyethyl acrylate degrades cell adhesion. Taking into consideration of this point, the founding of the present inventors that a copolymer formed by using the ethylenically unsaturated monomer having a carboxylic group can express excellent cell adhesion as compared to PTHFA is very surprising.

Hereinafter, a preferred embodiment of the present invention will be described. Incidentally, the present invention is not limited only to the following embodiment.

In the present description, the term "X to Y" which indicates a range means the term "X or more and Y or less" including X and Y. Further, unless otherwise specified, operations and measurements of physical properties and the like are conducted under conditions of room temperature (20 to 25° C.)/relative humidity of 40 to 50% RH.

<Cell Culture Substrate>

The cell culture substrate of the present invention comprises a coating layer containing the copolymer formed on at least one surface of a polymer substrate.

When the coating layer containing the copolymer according to the present invention is formed on a surface of a polymer substrate (particularly, a hydrophilic polymer substrate), excellent cell adhesion can be expressed as compared to the case of forming a coating layer containing PTHFA. Further, the cell culture substrate having the coating layer containing the copolymer according to the present invention is also excellent in cell extension ability (cell proliferation activity). In addition, the coating layer containing the copolymer according to the present invention can be simply formed in such a manner that the copolymer is dissolved in a solvent and the resultant solution is applied to a surface of the polymer substrate. Therefore, by using the copolymer according to the present invention, a coating layer having cell adhesion (and further cell proliferation activity) can be formed on a surface of cell culture substrate (cell culture vessel) regardless of its shape or design.

(Copolymer)

The copolymer according to the present invention has more than 40% by mole and less than 100% by mole of a structural unit (1) derived from furfuryl (meth)acrylate represented by the following Formula (1) and more than 0% by mole and less than 60% by mole of a structural unit (2) derived from ethylenically unsaturated monomer having a carboxylic group. Herein, the total of the structural unit (1) and the structural unit (2) is 100% by mole. By using the copolymer, as compared to the case of using PTHFA, excellent cell adhesion (and further cell proliferation activity) can be provided to a polymer substrate (particularly, a hydrophilic polymer substrate). In addition, by applying a solution of the copolymer to the surface of the polymer substrate, a coating layer can be simply formed even with respect to substrata having various shapes. Therefore, with the copolymer according to the present invention, a coating layer excellent in cell adhesion (and further cell proliferation activity) can be formed with respect to cell culture substrates (cell culture vessels) having various shapes or designs.

From the viewpoint of further improving cell adhesion (and further cell proliferation activity), it is preferable that the structural unit (1) is 50 to 98% by mole and the structural unit (2) is 2 to 50% by mole, with respect to the total of the structural unit (1) and the structural unit (2). It is more preferable that the structural unit (1) is 60 to 95% by mole and the structural unit (2) is 5 to 40% by mole, with respect to the total of the structural unit (1) and the structural unit (2). It is furthermore preferable that the structural unit (1) is 70 to 93% by mole and the structural unit (2) is 7 to 30% by mole, with respect to the total of the structural unit (1) and the structural unit (2). It is particularly preferable that the structural unit (1) is 80 to 90% by mole and the structural unit (2) is 10 to 20% by mole, with respect to the total of the structural unit (1) and the structural unit (2). It is most preferable that the structural unit (1) is 85 to 90% by mole and the structural unit (2) is 10 to 15% by mole, with respect to the total of the structural unit (1) and the structural unit (2).

That is, according to a preferred embodiment of the present invention, the copolymer is a copolymer having 50 to 98% by mole of the structural unit (1) and 2 to 50% by mole of the structural unit (2) (the total of the structural unit (1) and the structural unit (2) is 100% by mole). According to a more preferred embodiment of the present invention, the copolymer is a copolymer having 60 to 95% by mole of the structural unit (1) and 5 to 40% by mole of the structural unit (2) (the total of the structural unit (1) and the structural unit (2) is 100% by mole). According to a further more preferred embodiment of the present invention, the copolymer is a copolymer having 70 to 93% by mole of the structural unit (1) and 7 to 30% by mole of the structural unit (2) (the total of the structural unit (1) and the structural unit (2) is 100% by mole). According to a particularly preferred embodiment of the present invention, the copolymer is a copolymer having 80 to 90% by mole of the structural unit (1) and 10 to 20% by mole of the structural unit (2) (the total of the structural unit (1) and the structural unit (2) is 100% by mole). According to a most preferred embodiment of the present invention, the copolymer is a copolymer having 85 to 90% by mole of the structural unit (1) and 10 to 15% by mole of the structural unit (2) (the total of the structural unit (1) and the structural unit (2) is 100% by mole).

The copolymer according to the present invention essentially includes the structural unit (1) and the structural unit (2), but may further have a structural unit derived from other monomer in addition to the structural unit (1) and the structural unit (2). Here, other monomer is not particularly limited as long as it does not inhibit cell adhesion. Specific examples of the another monomer include acrylamide, N,N- dimethylacrylamide, N,N-diethylacrylamide, methacrylamide, N,N-dimethylmethacrylamide, N,N-diethylmethacrylamide, ethylene, propylene, N-vinylacetamide, N-isopropenyl acetamide, N-(meth)acryloyl morpholine, and the like. These other monomers may be used singly or in combination of two or more kinds thereof. The composition of the structural unit derived from other monomer in a case where the copolymer further has a structural unit derived from other monomer is not particularly limited as long as it does not inhibit cell adhesion, but the structural unit derived from other monomer is preferably more than 0% by mole and less than 10% by mole and more preferably about 3 to 8% by mole with respect to the total of the structural unit (1) and the structural unit (2).

However, from the viewpoint of further improving cell adhesion (and further cell proliferation activity), it is preferable that the copolymer does not include a structural unit derived from other monomer, that is, is configured by only the structural unit (1) and the structural unit (2). That is, according to a preferred embodiment of the present invention, the copolymer is composed of the structural unit (1) and the structural unit (2).

Therefore, according to a more preferred embodiment of the present invention, the copolymer is a copolymer configured by 50 to 98% by mole of the structural unit (1) and 2 to 50% by mole of the structural unit (2) (the total of the structural unit (1) and the structural unit (2) is 100% by mole). According to a further preferred embodiment of the present invention, the copolymer is a copolymer configured by 60 to 95% by mole of the structural unit (1) and 5 to 40% by mole of the structural unit (2) (the total of the structural unit (1) and the structural unit (2) is 100% by mole). According to a further more preferred embodiment of the present invention, the copolymer is a copolymer configured by 70 to 93% by mole of the structural unit (1) and 7 to 30% by mole of the structural unit (2) (the total of the structural unit (1) and the structural unit (2) is 100% by mole). According to a particularly preferred embodiment of the present invention, the copolymer is a copolymer configured by 80 to 90% by mole of the structural unit (1) and 10 to 20% by mole of the structural unit (2) (the total of the structural unit (1) and the structural unit (2) is 100% by mole). According to a most preferred embodiment of the present invention, the copolymer is a copolymer configured by 85 to 90% by mole of the structural unit (1) and 10 to 15% by mole of the structural unit (2) (the total of the structural unit (1) and the structural unit (2) is 100% by mole).

Incidentally, the content (% by mole) of the structural unit (1) with respect to the total of the structural unit (1) and the structural unit (2) is substantially the same as the content (% by mole) of furfuryl (meth)acrylate with respect to the total amount of furfuryl (meth)acrylate and the ethylenically unsaturated monomer having a carboxylic group used in synthesis of the copolymer. Further, the content (% by mole) of the structural unit (2) with respect to the total of the structural unit (1) and the structural unit (2) is substantially the same as the content (% by mole) of the ethylenically unsaturated monomer having a carboxylic group with respect to the total amount of furfuryl (meth)acrylate and the ethylenically unsaturated monomer having a carboxylic group used in synthesis of the copolymer.

In the copolymer according to the present invention, the arrangement of each structural unit is not particularly limited. The copolymer according to the present invention may be in the form of block (block copolymer), random (random copolymer), or alternate (alternate copolymer).

<<Structural Unit (1)>>

The structural unit (1) is derived from furfuryl (meth)acrylate of the following Formula (1). The structural unit (1) constituting the copolymer may be one kind alone or a combination of two or more kinds. That is, the structural unit (1) may be configured by only one kind of the structural unit derived from furfuryl (meth)acrylate of the following Formula (1) or may be configured by two or more kinds of the structural units derived from furfuryl (meth)acrylate of the following Formula (1). In the latter case, each structural unit may be present in the form of block or random. Further, in a case where the structural unit (1) is configured by two or more kinds of the structural units derived from furfuryl (meth)acrylate of the following Formula (1), the composition of the structural unit (1) is the total ratio (molar ratio (% by mole)) of the furfuryl (meth)acrylate-derived structural units with respect to the total of the structural unit (1) and the structural unit (2).

[Chemical Formula 5]

[Chemical Formula 6]

Formula (1)

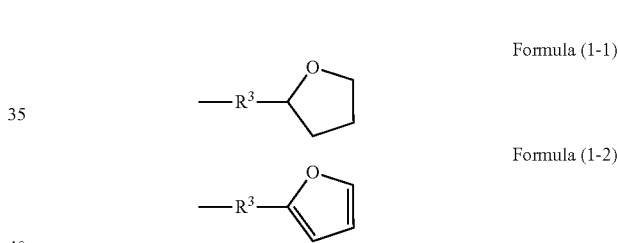

Formula (1-1)

Formula (1-2)

In the Formula (1), $R^1$ is a hydrogen atom or a methyl group.

$R^2$ represents a group represented by the above Formula (1-1) or Formula (1-2). Of them, from the viewpoint of further improvement in cell adhesion (and further cell proliferation activity), and the like, $R^2$ preferably represents a group represented by the above Formula (1-1). In the above Formulae (1-1) and (1-2), $R^3$ represents an alkylene group having 1 to 3 carbon atoms. Herein, as the alkylene group having 1 to 3 carbon atoms, there are a methylene group ($-CH_2-$), an ethylene group ($-CH_2CH_2-$), a trimethylene group ($-CH_2CH_2CH_2-$), and a propylene group ($-CH(CHOCH_2-$ or $-CH_2CH(CH_3)-$). Of them, from the viewpoint of further improving cell adhesion (and further cell proliferation activity), $R^3$ preferably represents a methylene group ($-CH_2-$) or an ethylene group ($-CH_2CH_2-$) and more preferably represents a methylene group ($-CH_2-$).

That is, as the furfuryl (meth)acrylate, there are tetrahydrofurfuryl acrylate, tetrahydrofurfuryl methacrylate, furfuryl acrylate, furfuryl methacrylate, 5-[2-(acryloyloxy)ethyl]tetrahydrofuran, 5-[2-(methacryloyloxy)ethyl]tetrahydrofuran, 5-[2-(acryloyloxy)ethyl]furane, 5-[2-(methacryloyloxy)ethyl]furane, and the like. These may be used singly or in combination of two or more kinds thereof. Of them, from the viewpoint of further improving cell adhesion (and further cell proliferation activity), tetrahydrofurfuryl (meth)acrylate is preferred and tetrahydrofurfuryl acrylate (THFA) is more preferred.

<<Structural Unit (2)>>

The structural unit (2) is derived from an ethylenically unsaturated monomer having a carboxylic group. The structural unit (2) constituting the copolymer may be one kind alone or a combination of two or more kinds. That is, the structural unit (2) may be configured by only one kind of the structural unit derived from ethylenically unsaturated monomer having a carboxylic group or may be configured by two or more kinds of the structural units derived from ethylenically unsaturated monomer. In the latter case, each structural unit may be present in the form of block or random. Further, in a case where structural unit (2) is configured by two or more kinds of the structural units derived from ethylenically unsaturated monomer having a carboxylic group, the composition of the structural unit (2) is the total ratio (molar ratio (% by mole)) of the structural units derived from ethylenically unsaturated monomer having a carboxylic group with respect to the total of the structural unit (1) and the structural unit (2).

The ethylenically unsaturated monomer having a carboxylic group which forms the structural unit (2) is not particularly limited as long as it is a compound having one or more carboxylic groups (—COOH) and one or more ethylenically unsaturated groups in one molecule. Herein, the "ethylenically unsaturated group" refers to a group in which a hydrogen atom of ethylene ($CH_2=CH_2$) is substituted, and examples thereof include a (meth)acryloyl group, a vinyl group, an allyl group, a vinyl ether group, and the like. Incidentally, only one of these groups may be contained in one molecule of the ethylenically unsaturated monomer or two or more groups may be contained.

Of them, as the ethylenically unsaturated group, a (meth)acryloyl group is preferred. That is, according to a preferred embodiment of the present invention, the ethylenically unsaturated monomer has a (meth)acryloyl group. Thus, the ethylenically unsaturated monomer is preferably a compound having one or more carboxylic groups and one or more acryloyl groups or methacryloyl groups in one molecule. The upper limit of the number of carboxylic groups and (meth)acryloyl groups contained in the ethylenically unsaturated monomer is not particularly limited, but from the viewpoint of cell adhesion (and further cell proliferation activity), the number of carboxylic groups in one molecule is preferably 3 or less, more preferably 2 or less, and particularly preferably 1. Further, from the viewpoint of the ease of preparation of the copolymer with furfuryl (meth)acrylate represented by the above Formula (1), and control of cell adhesion (and further cell proliferation activity), the number of (meth)acryloyl groups in one molecule is preferably 3 or less and more preferably 2 or less. In particular, from the viewpoint of controlling the composition (molar ratio) of each structural unit to further improve cell adhesion (and further cell proliferation activity), the number of (meth)acryloyl groups in one molecule is particularly preferably 1.

From the viewpoint of further improving cell adhesion (and further cell proliferation activity), it is preferable that the structural unit (2) is derived from carboxyalkyl (meth)acrylate represented by the following Formula (2). That is, the ethylenically unsaturated monomer is preferably carboxyalkyl (meth)acrylate represented by the following Formula (2). The structural unit (2) constituting the copolymer may be one kind alone or a combination of two or more kinds. That is, the structural unit (2) may be configured by only one kind of the structural unit derived from carboxyalkyl (meth)acrylate represented by the following Formula (2) or may be configured by two or more kinds of the structural units derived from carboxyalkyl (meth)acrylate represented by the following Formula (2). In the latter case, each structural unit may be present in the form of block or random. Further, in a case where the structural unit (2) is configured by two or more kinds of the structural units derived from carboxyalkyl (meth)acrylate represented by the following Formula (2), the composition of the structural unit (2) is the total ratio (molar ratio (% by mole)) of the carboxyalkyl (meth)acrylate-derived structural units with respect to the total of the structural unit (1) and the structural unit (2).

[Chemical Formula 7]

Formula (2)

In the above Formula (2), $R^4$ represents a hydrogen atom or a methyl group and preferably represents a hydrogen atom. $R^5$ is an alkylene group having 2 or 3 carbon atoms. Herein, as the alkylene group having 2 or 3 carbon atoms, there are an ethylene group (—$CH_2CH_2$—), a trimethylene group (—$CH_2CH_2CH_2$—), and a propylene group (—CH($CH_3$)$CH_2$— or —$CH_2$CH($CH_3$)—). Among these, from the viewpoint of further improving cell adhesion (and further cell proliferation activity), or the like, $R^5$ preferably represents an ethylene group (—$CH_2CH_2$—) or a trimethylene group (—$CH_2CH_2CH_2$—), and more preferably an ethylene group (—$CH_2CH_2$—).

Specifically, examples of the carboxyalkyl (meth)acrylate include carboxyethyl acrylate, carboxypropyl acrylate, carboxyisopropyl acrylate, carboxyethyl methacrylate, carboxy propyl methacrylate, carboxyisopropyl methacrylate, and the like. These may be used singly or in combination of two or more kinds thereof. Among these, from the viewpoint of further improving cell adhesion (and further cell proliferation activity), or the like, carboxyethyl (meth)acrylate is preferable, and carboxyethyl acrylate (CEA) is more preferable.

The weight average molecular weight (Mw) of the copolymer is not particularly limited, and is preferably 5,000 to 200,000. Within the above range, the solubility of the copolymer in a solvent can be improved and application to a substrate can be uniformly conducted with ease. From the viewpoint of improving coating film formability, the weight average molecular weight of the copolymer is more preferably 10,000 to 100,000 and particularly preferably 14,000 to 50,000.

In the present description, as the "weight average molecular weight (Mw)," a value measured by gel permeation chromatography (GPC) using polystyrene as a standard substance and tetrahydrofuran (THF) as a mobile phase respectively is adopted. Specifically, the copolymer is dissolved in tetrahydrofuran (THF) so as to have a concentration of 10 mg/ml, thereby preparing a sample. Regarding the sample prepared as above, GPC column LF-804 (manufactured by Showa Denko K.K.) is attached to a GPC system LC-20 (manufactured by SHIMADZU CORPORATION), THF is supplied as a mobile phase, and polystyrene is used as a standard, to measure GPC of the copolymer. After preparing a calibration curve with polystyrene as standards, the weight average molecular weight (Mw) of the copolymer is calculated on the basis of the curve.

The copolymer according to the present invention can be produced by employing a conventionally known polymerization method such as bulk polymerization, suspension polymerization, emulsion polymerization, solution polymerization, living radical polymerization method, polymerization method using a macroinitiator, polycondensation method, or the like, for example, although not particularly limited thereto. Specifically, in a case where the copolymer according to the present invention is a block copolymer, for example, a living radical polymerization method or a polymerization method using a macroinitiator is preferably used. As the living radical polymerization method, although not particularly limited thereto, a method described in JP H11-263819 A, JP 2002-145971 A, JP 2006-316169 A, or the like, an atom transfer radical polymerization (ATRP) method, and the like can be applied similarly or appropriately modified, for example.

Alternatively, for example, in a case where the copolymer according to the present invention is a random copolymer, it is preferable to use a method of stirring the furfuryl (meth)acrylate of the above Formula (1), the ethylenically unsaturated monomer having a carboxylic group (preferably, the carboxyalkyl (meth)acrylate of the above Formula (2)), and as necessary, one or two or more kinds of monomer which is copolymerizable with those components (other monomer, copolymerizable monomer; the same applies hereinafter), in a polymerization solvent, with a polymerization initiator to prepare a monomer solution, and heating the monomer solution to perform copolymerization. In the method, a polymerization solvent which can be used in the preparation of the monomer solution is not particularly limited as long as it can dissolve the monomer used above. Examples thereof include aqueous solvents such as water, alcohol such as methanol, ethanol, propanol, or isopropanol, and polyethylene glycols; aromatic solvents such as toluene, xylene, and tetralin; halogen-based solvents such as chloroform, dichloroethane, chlorobenzene, dichlorobenzene, and trichlorobenzene; and the like. Among these, taking in consideration of easy dissolution of the monomer, or the like, methanol or ethanol is preferable. Further, a concentration of the monomer in the monomer solution is not particularly limited, but the concentration of the monomer in the monomer solution is typically 15 to 60% by weight, more preferably 20 to 50% by weight, and particularly preferably 25 to 45% by weight. Incidentally, the concentration of the monomer means the total concentration of the furfuryl (meth)acrylate of the above Formula (1), the ethylenically unsaturated monomer having a carboxylic group (preferably, the carboxyalkyl (meth)acrylate of the above Formula (2)), and if being used, a monomer which is copolymerizable with those components (other monomer, copolymerizable monomer).

The polymerization initiator is not particularly limited, and a known polymerization initiator may be used. From the viewpoint of high polymerization stability, the polymerization initiator is preferably a radical polymerization initiator. Specific examples thereof include persulfates such as potassium persulfate (KPS), sodium persulfate, and ammonium persulfate; peroxides such as hydrogen peroxide, t-butyl peroxide, and methyl ethyl ketone peroxide; and azo compounds such as azobisisobutyronitrile (AIBN), 2,2'-azobis(4-methoxy-2,4-dimethylvaleronitrile), 2,2'-azobis(2,4-dimethylvaleronitrile), 2,2'-azobis[2-(2-imidazoline-2-yl)propane]dihydrochloride, 2,2'-azobis[2-(2-imidazoline-2-yl)propane]disulfate dihydrate, 2,2'-azobis(2-methylpropionamidine)dihydrochloride, 2,2'-azobis[N-(2-carboxyethyl)-2-methylpropionamidine)]hydrate, 3-hydroxy-1,1-dimethylbutyl peroxyneodecanoate, α-cumylperoxy neod- ecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl)peroxydicarbonate, di(secondary butyl)peroxydicarbonate, and azobiscyanovaleric acid. Further, for example, a reducing agent such as sodium sulfite, sodium hydrogen sulfite, or ascorbic acid may be used in combination with the radical polymerization initiator as a redox type initiator. The blending amount of the polymerization initiator is preferably 0.5 to 5 mmol with respect to 1 mol of the total amount of the monomer. With such a blending amount of the polymerization initiator, copolymerization of the respective monomers can efficiently proceed.

The polymerization initiator as it is may be mixed with the furfuryl (meth)acrylate of the above Formula (1), the ethylenically unsaturated monomer having a carboxylic group (preferably, the carboxyalkyl (meth)acrylate of the above Formula (2)), and if being used, a monomer which is copolymerizable with those components (other monomer, copolymerizable monomer), and a polymerization solvent, or the initiator in a solution state obtained by the initiator dissolved in another solvent in advance may be mixed with the monomers and the polymerization solvent. In the latter case, another solvent used to dissolve the polymerization initiator is not particularly limited as long as it can dissolve the polymerization initiator, but the same solvent as the polymerization solvent described above can be exemplified. Further, another solvent may be the same as or different from the polymerization solvent, but in consideration of easy control of polymerization, and the like, the same solvent as the polymerization solvent is preferably used. Further, in this case, a concentration of the polymerization initiator in another solvent is not particularly limited, but in consideration of easy mixing, and the like, the addition amount of the polymerization initiator is preferably 0.1 to 10 parts by weight and more preferably 0.5 to 5 parts by weight, with respect to 100 parts by weight of another solvent.

Further, in the case of using the polymerization initiator in the solution state, a deaeration treatment may be performed in advance before adding a solution in which the monomers (furfuryl (meth)acrylate, ethylenically unsaturated monomer having a carboxylic group, and a copolymerizable monomer which is used optionally) are dissolved in the polymerization solvent, to the polymerization initiator solution. For the deaeration treatment, for example, the solution may be bubbled with an inert gas such as nitrogen gas or argon gas for about 0.5 to 5 hours. In the deaeration treatment, the solution may be adjusted to about 30° C. to 80° C., preferably to a polymerization temperature in a polymerization step as described below.

Next, the monomer solution is heated to copolymerize the respective monomers. Here, as the copolymerization method, for example, a known polymerization method such as radical polymerization, anionic polymerization, or cationic polymerization can be adopted, and radical polymerization which facilitates production is preferably used.

The polymerization conditions are not particularly limited as long as the furfuryl (meth)acrylate of the above Formula (1), the ethylenically unsaturated monomer having a carboxylic group (preferably, the carboxyalkyl (meth)acrylate of the above Formula (2)), and if being used, a monomer which is copolymerizable with those components (other monomer, copolymerizable monomer)) can be copolymerized. Specifically, the copolymerization temperature is preferably 30 to 80° C. and more preferably 40° C. to 55° C. Further, the copolymerization time is preferably is 1 to 24 hours and more preferably 5 to 12 hours. Under such conditions, copolymerization of the respective monomers can efficiently proceed. Further, it is possible to effectively suppress or prevent gelation in the polymerization step and to achieve high production efficiency.

As necessary, a chain transfer agent, a polymerization rate-adjusting agent, a surfactant, and other additives may be appropriately used during the polymerization.

An atmosphere under which the polymerization reaction is carried out is not particularly limited, and the reaction can be carried out under an air atmosphere, an inert gas atmosphere such as nitrogen gas or argon gas, and the like. Further, during the polymerization reaction, the reaction solution may be stirred.

The polymer after polymerization can be purified by a general purification method such as a reprecipitation method (precipitation method), a dialysis method, an ultrafiltration method, or an extraction method.

The purified polymer can be dried by an arbitrary method such as freeze drying, vacuum drying, spray drying, or heat drying, but freeze drying or vacuum drying is preferred from the viewpoint that the physical properties of the polymer are less affected.

(Polymer Substrate)

In the present invention, a coating layer containing the copolymer is formed on at least one side of the polymer substrate. Herein, the coating layer is formed on at least a surface of the polymer substrate with which cells contact (for example, on which a liquid containing cells flows or cells are cultured). Further, it is not necessary to form the coating layer on an entire surface of the polymer substrate. The coating layer may be formed on a portion (a part) of the surface of the polymer substrate with which cells contact (for example, on which a liquid containing cells flows or cells are cultured), but from the viewpoint of further improving cell adhesion (and further cell proliferation activity), the coating layer is preferably formed on the entire surface of the polymer substrate at the side with which cells contact (for example, on which a liquid containing cells flows or cells are cultured).

A material constituting the polymer substrate is not particularly limited, and examples thereof include hydrophobic polymers such as polyamide (PA), polyaramide (PAA), polyethersulfone (PES), polyarylethersulfone (PAES), polysulfone (PSU), polyarylsulphone (PASU), polycarbonate (PC), polyether, polyurethane (PUR), polyetherimide, polypropylene, polyethylene, polystyrene, polyacrylonitrile, and polytetrafluoroethylene; hydrophilic polymers such as polyvinylpyrrolidone (PVP), polyethylene glycol (PEG), polyglycolmonoester, water soluble cellulosic derivatives, polysorbate, and polyethylene-polypropylene oxide copolymers; and the like. The hydrophobic polymer may be used singly or as a mixture of two or more kinds thereof. The hydrophilic polymer may be used singly or as a mixture of two or more kinds thereof.

In an embodiment of the present invention, the polymer substrate preferably contains at least one selected from the group consisting of polyamide (PA), polyethersulfone (PES), polyarylethersulfone (PAES), and polyvinylpyrrolidone (PVP). Such a polymer substrate is suitably used as a hollow fiber membrane of a bioreactor.

The polymer substrate according to the present invention may be a mixture of the hydrophobic polymer and the hydrophilic polymer, for example, a mixture of polyamide (PA), polyarylethersulfone (PAES), and polyvinylpyrrolidone (PVP). Such a polymer substrate is particularly suitably used as a hollow fiber membrane of a bioreactor. In a case where the polymer substrate is a mixture of the hydrophobic polymer and the hydrophilic polymer, for example, the content of the hydrophobic polymer is 65 to 95% by weight and the content of the hydrophilic polymer is 5 to 35% by weight, with respect to the total amount of the hydrophobic polymer and the hydrophilic polymer.

The structure of the polymer substrate is not limited, and in addition to the plane structure, the polymer substrate can be designed in various structures (forms) such as a structure in which a porous body is inserted, a hollow fiber structure, a porous membrane structure, a sponge structure, and a flocculent (glass wool) structure. As described later, the cell culture substrate of the present invention can be suitably used in a bioreactor, particularly, a hollow fiber type bioreactor. Therefore, the polymer substrate preferably has hollow fibers and is more preferably a porous membrane (hollow fiber membrane) formed of a plurality of hollow fibers.

The inner diameter (diameter) of the hollow fibers is not particularly limited, but is preferably 50 to 1,000 μm, more preferably 100 to 500 μm, and particularly preferably about 150 to 350 μm. Further, the outer diameter (diameter) of the hollow fibers is not particularly limited, but is preferably 100 to 1,200 μm, more preferably 150 to 700 μm, and particularly preferably about 200 to 500 μm. The length of the hollow fibers is not particularly limited, but is preferably 50 to 900 mm, more preferably 100 to 700 mm, and particularly preferably about 150 to 500 mm. The number of the hollow fibers constituting the hollow fiber membrane is not particularly limited, but is, for example, about 1,000 to 100,000, more preferably 3,000 to 50,000, and particularly preferably about 5,000 to 25,000. In an embodiment, the polymer substrate is configured by about 9,000 hollow fibers having an average length of about 295 mm, an average inner diameter of 215 μm, and an average outer diameter of 315 μm. Herein, the coating layer may be formed on the inner side or the outer side of the hollow fiber membrane, but is preferably formed on the inner (lumen) surface.

The outer layer of the hollow fiber may have an open pore structure with a certain surface roughness. An opening (diameter) of the pore is not particularly limited, but is in the range of about 0.5 to about 3 μm, and the number of pores on the outer surface of the hollow fiber may be in the range of about 10,000 to about 150,000 per 1 square millimeter (1 $mm^2$). A thickness of the outer layer of the hollow fiber is not particularly limited, and for example, is in the range of about 1 to about 10 μm. The hollow fiber may have an additional layer (second layer) on the outer side, and at this time, the additional layer (second layer) preferably has a sponge structure having a thickness of about 1 to about 15 μm. The second layer having such a structure can serve as a support for the outer layer. Further, in this embodiment, the hollow fiber may have a further additional layer (third layer) at the outer side of the second layer. In this embodiment, the further additional layer (third layer) preferably has a finger-like structure. With the third layer having such a structure, mechanical stability is obtainable. Further, a high void volume with low resistance to membrane transfer of molecules can be provided. In this embodiment, during use, the finger-like voids are filled with fluid and the fluid gives a lower resistance for diffusion and convection than a matrix with a sponge-filled structure having a lower void volume. This third layer has a thickness of, preferably, about 20 to about 60 μm.

A method for producing a hollow fiber and a porous membrane is not particularly limited, and a known production method can be applied similarly or appropriately modified. For example, it is preferable that micro fine holes are formed on a wall of hollow fiber by a stretching method or a solid-liquid phase separation method.

The hollow fiber membrane used in a bioreactor is typically subjected to a hydrophilization treatment for performing culture medium replacement inside or outside the hollow fiber membrane. However, in a case where cells are cultured using such a hydrophilic polymer substrate, since a cell adhesion factor (cell-adhesive protein) contained in the culture medium is hardly adsorbed to the substratum, cell adhesion is poor. In this regard, when the surface treatment of the hydrophilic polymer substrate is performed using the copolymer, its surface is moderately hydrophobized (for example, the contact angle to water becomes about 60 to 70°), so that the cell adhesion factor is easily adsorbed. Further, the carboxyl group contained in the copolymer is presumed to promote extension (proliferation) or adhesion of cells via activation or induction of signals of extension (proliferation) of cells or adhesion of cells. Further, when the copolymer is coated on the hydrophilic polymer substrate, the carboxyl group are easily oriented on the coating layer to be formed, so that adhesion or extension (proliferation) of cells is further promoted. Therefore, when the surface of the hydrophilic polymer substrate is coated with the copolymer, cell adhesion and further cell extension (proliferation) ability are considered to be improved. That is, in an embodiment of the present invention, the polymer substrate is a hydrophilic polymer substrate.

The method for producing the hydrophilic polymer substrate is not particularly limited, and examples thereof include (i) a method in which a polymer substrate is produced using the hydrophilic polymer or using a mixture of the hydrophobic polymer and the hydrophilic polymer by a conventionally known method, (ii) a method in which a polymer substrate is produced using the hydrophobic polymer or using a mixture of the hydrophobic polymer and the hydrophilic polymer by a conventionally known method and then a surface of the polymer substrate is hydrophilized using a known means such as a plasma treatment, a corona treatment, or a primer treatment, and the like.

Alternatively, the polymer substrate according to the present invention may be hydrophobic polymer substrate (for example, a polymer substrate having a surface having a contact angle to water of 80° or more). In the case of culturing cells using the hydrophobic polymer substrate, albumin abundantly contained in the culture medium is adsorbed to the substrate. Since albumin does not have a cell adhesion site, cells are hardly attached to the substrate covered with albumin. Here, when the surface treatment of the hydrophobic polymer substrate is performed using the copolymer, the surface of the substrate is moderately hydrophilized (for example, the contact angle to water becomes about 60 to 70°) and the cell adhesion factor is easily adsorbed. Further, the carboxyl group contained in the copolymer is presumed to promote extension (proliferation) or adhesion of cells via activation or induction of signals of extension (proliferation) of cells or adhesion of cells. Therefore, when the surface of the hydrophobic polymer substrate is coated with the copolymer, cell adhesion and further cell extension (proliferation) ability are considered to be improved.

The method for producing a hydrophobic polymer substrate is not particularly limited, and for example, a polymer substrate can be produced by a conventionally known method using the hydrophobic polymer as a raw material.

As the polymer substrate, commercially available products may be used, and examples thereof include Polyflux (registered trademark) manufactured by Baxter Limited, Desmopan (registered trademark) manufactured by DIC Covestro Polymer Ltd., and the like.

(Method of Forming Coating Layer)

A method of forming a coating layer containing the copolymer according to the present invention on a surface of the polymer substrate is not particularly limited. For example, in a case where the surface of the polymer substrate has a flat dish (plate) structure, a method of applying a copolymer-containing solution obtained by dissolving the copolymer according to the present invention to a predetermined surface (for example, by adding to a well) and then drying coating film can be used. Further, for example, in a case where the polymer substrate is a hollow fiber or a porous membrane, a method of bringing a copolymer-containing solution obtained by dissolving the copolymer according to the present invention into contact with a cell contact portion of the hollow fiber (for example, by flowing on an inner surface (lumen) or an outer surface of the hollow fiber) and then drying coating film can be used. Incidentally, in a case where the polymer substrate is a porous membrane formed by a plurality of hollow fibers, coating with a copolymer-containing solution may be performed with respect to one hollow fiber and then the hollow fibers may be bundled, or a plurality of hollow fibers are bundled to produce a porous membrane and then the coating may be performed.

Herein, a solvent for dissolving the copolymer according to the present invention is not particularly limited as long as it can dissolve the copolymer according to the present invention. From the viewpoint of solubility of the copolymer, and the like, for example, aqueous solvents such as water, alcohol such as methanol, ethanol, propanol, or isopropanol, and polyethylene glycols; ketone-based solvents such as acetone; furan-based solvents such as tetrahydrofuran; and the like are exemplified. The solvent may be used singly or in the form of a mixture of two or more kinds thereof. Among these, in consideration of further improvement in solubility of the copolymer according to the present invention, the solvent is preferably a mixed solvent of water and alcohol. The alcohol used in the mixed solvent is preferably lower alcohol having 1 to 4 carbon atoms from the viewpoint of improving solubility of the copolymer, particularly, methanol or ethanol is preferred and ethanol is particularly preferred. That is, the solvent is preferably configured by water and ethanol. Herein, the mixing ratio of water and ethanol is not particularly limited, and for example, the mixing ratio (volume ratio) of water and ethanol is preferably 1:1 to 50 and more preferably 1:5 to 15. A concentration of the copolymer in the copolymer-containing solution is not particularly limited. In consideration of the ease of application to the substrate, the effect of reducing coating unevenness, and the like, the concentration thereof is preferably 0.0001 to 5% by weight more preferably 0.001 to 2% by weight.

Further, a method of coating the copolymer is not particularly limited, and a conventionally known method such as filling, dip coating (immersion method), spraying, spin coating, dropping, doctor blade, brush coating, roll coater, air knife coating, curtain coating, wire bar coating, gravure coating, or mixed solution-impregnated sponge coating can be applied.

Further, conditions for forming the coating film of the copolymer are not particularly limited. For example, a contact time of the copolymer-containing solution and the polymer substrate (for example, a time for circulating the copolymer-containing solution to a lumen or an outer surface of the hollow fiber) is preferably 1 to 5 minutes and more preferably 1 to 3 minutes, in consideration of the easy formation of the coating film (thus coating layer), the effect of reducing coating unevenness, and the like. Further, a contact temperature of the copolymer-containing solution and the polymer substrate (for example, a temperature at which the copolymer-containing solution is circulated to a lumen or an outer surface of hollow fiber) is preferably 5 to 40° C. and more preferably 15 to 30° C., in consideration of the easy formation of the coating film (thus coating layer), the effect of reducing coating unevenness, and the like.

The amount of the copolymer-containing solution applied to the surface of the polymer substrate is not particularly limited, but is preferably such an amount that the thickness of the coating layer after drying is in a range described later. Incidentally, in a case where the above-described thickness is not obtainable by single contact (application), a contact (application) step (or the application step and a drying step described later) may be repeated until a desired thickness is obtainable.

Next, by drying the coating film after the contact of the polymer substrate and the copolymer-containing solution, the coating layer (coating film) by the copolymer according to the present invention is formed on the surface of the polymer substrate. Herein, drying conditions are not particularly limited as long as the coating layer (coating film) of the copolymer according to the present invention can be formed. Specifically, a drying temperature is preferably 5 to 50° C. and more preferably 15 to 40° C. A drying step may be performed under a single condition or may be performed stepwise under different conditions. Further, a drying time is not particularly limited, but is, for example, about 1 to 60 hours. Further, in a case where the polymer substrate is a porous membrane (hollow fiber membrane), the coating film may be dried by allowing a gas of 5 to 40° C. and more preferably 15 to 30° C. to continuously or gradually circulate on a surface of hollow fiber to which the copolymer-containing solution is applied. Herein, the gas is not particularly limited as long as it has no influence on the coating film (coating layer) and can dry the coating film. Specific examples thereof include air, an inert gas such as nitrogen gas or argon gas, and the like. Further, a circulation amount of the gas is not particularly limited as long as the coating film can be sufficiently dried. The circulation amount of the gas is preferably 5 to 150 L/min and more preferably 30 to 100 L/min.

According to such a method, a coating layer containing the copolymer according to the present invention can be efficiently formed on the polymer substrate. Incidentally, depending on the type of cells to be adhered, the polymer substrate may be further treated with a cell adhesion factor such as fibronectin, laminin, or collagen. With such a treatment, adhesion of cells to the substrate surface and growth of cells can be further promoted. In a case where the polymer substrate is a porous membrane formed of a plurality of hollow fibers, the treatment with a cell adhesion factor may be performed with respect to one hollow fiber and then the hollow fibers may be bundled, or a plurality of hollow fibers are bundled to produce a porous membrane and then the treatment may be performed. Further, the treatment with a cell adhesion factor may be performed after the coating layer containing the copolymer according to the present invention is formed, before the coating layer containing the copolymer according to the present invention is formed, or at the same time the coating layer containing the copolymer according to the present invention is formed.

In the present invention, the thickness (dry thickness) of the coating layer formed on the polymer substrate is preferably 0.005 to 20 μm.

<Bioreactor>

The cell culture substrate of the present invention is excellent in cell adhesion (and further cell proliferation activity). Therefore, the cell culture substrate of the present invention can be suitably used in a bioreactor. That is, the present invention provides a bioreactor including the cell culture substrate of the present invention. Here, the bioreactor may be a plane type bioreactor or a hollow fiber type bioreactor, but is particularly preferably a hollow fiber type bioreactor. Therefore, in the following description, although a hollow fiber type bioreactor will be described as a preferred embodiment, the bioreactor of the present invention may be a plane type bioreactor, and in this case, the following embodiment can be appropriately changed and applied. Further, dimensional ratios in the drawings are exaggerated for the sake of explanatory convenience and may differ from actual ratios.

The bioreactor in which the cell culture substrate of the present invention can be suitably used is not particularly limited, but the cell culture substrate and the bioreactor of the present invention can be applied, for example, to cell culture/expansion systems described in JP 2010-523118 A (JP 5524824 B2) (WO 2008/124229 A2), JP 2013-524854 A (JP 6039547 B2) (WO 2011/140231 A1), JP 2013-507143 A (JP 5819835 B2) (WO 2011/045644 A1), JP 2013-176377 A (WO 2008/109674), JP 2015-526093 A (WO 2014/031666 A1), JP 2016-537001 A (WO 2015/073918 A1), JP 2017-509344 A (WO 2015/148704 A1), and the like; and Quantum Cell Expansion System manufactured by TERUMO BCT, INC. Conventionally, in the cell culture, facilities such as an incubator, a safety cabinet, and a clean room are separately needed, but the culture system as described above has all of those functions so that the facilities can be very simplified. Further, by controlling temperature or gas during the cell culture using the system as described above, a functionally closed system can be ensured and the cell culture can be performed automatically and in a closed environment.

Hereinafter, an embodiment of the bioreactor of the present invention will be described with reference to the drawings, but the present invention is not limited to the following embodiment.

Figure 2:
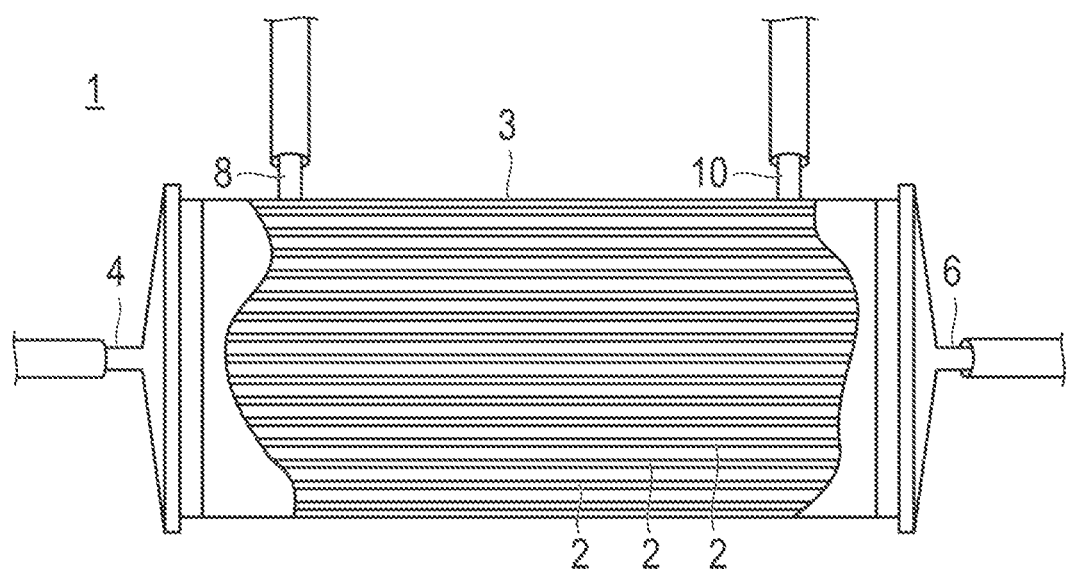
FIG. 2 is a partially cut-away side view of the bioreactor of FIG. 1.

FIG. 1 is a partial side view illustrating an embodiment of a bioreactor (hollow fiber type bioreactor) of the present invention. Further, FIG. 2 is a partially cut-away side view of the bioreactor of FIG. 1. In FIGS. 1 and 2, a bioreactor 1 has a cell culture substrate 2 of the present invention provided in a cell culture chamber 3. The cell culture chamber 3 has four openings, that is, four ports (an inlet port 4, an outlet port 6, an inlet port 8, and an outlet port 10). Herein, a culture medium including cells flows to a hollow fiber intracapillary (IC) space of the cell culture substrate 2 in the cell culture chamber 3 through the inlet port 4, and discharged from the outlet port 6. According to this, cells are efficiently adhered (attached) to and cultured on the surface of the hollow fiber lumen. Meanwhile, a culture medium or gas (such as oxygen or carbon dioxide) flows to be in contact with a hollow fiber extracapillary (EC) space of the cell culture substrate 2 in the cell culture chamber 3 through the inlet port 8, and discharged from the outlet port 10. According to this, in the cell culture chamber 3, small molecules such as culture medium components flow into the hollow fibers or unnecessary components are discharged from the inside of the hollow fibers, and cells adhered onto the surface of the hollow fibers are cultured. Further, after culturing for a predetermined time, a liquid (for example, PBS) containing trypsin is introduced into the intracapillary (IC) space of the hollow fiber of the cell culture substrate 2 in the cell culture chamber 3 through the inlet port 4, and then is held for a predetermined time (for example, about 5 to 10 minutes). Next, a culture medium or an isotonic solution such as PBS flows in the intracapillary (IC) space of the hollow fiber of the cell culture substrate 2 in the cell culture chamber 3 through the inlet port 4 to apply a shear force to cells, the cells are released from the inner wall of the hollow fiber, and the cells are recovered from the bioreactor through the outlet port 6. Incidentally, although the cells are adhered to the intracapillary (IC) space of the hollow fiber in the above embodiment, the present invention is not limited to the above embodiment, and cells may be cultured in such a manner that a culture medium containing cells flows into the outlet port 10 from the inlet port 8, the cells are efficiently adhered (attached) to an outer surface of the hollow fiber, and the culture medium flows into the outlet port 6 from the inlet port 4 in an hollow fiber lumen. Further, the fluid from the inlet port 4 into the outlet port 6 may flow in either a co-current or counter-current direction with respect to flow of fluid into the outlet port 10 from the inlet port 8.

(Use of Bioreactor)

As mentioned above, the bioreactor of the present invention includes a cell culture substrate excellent in cell adhesion (and further cell proliferation activity). Herein, cells which can be cultured in the bioreactor of the present invention may be adherent (scaffold-dependent) cells, non-adherent cells, or any combination thereof, but since the bioreactor is provided with the cell culture substrate excellent in cell adhesion, the bioreactor of the present invention can be particularly suitably used in culturing of adherent (scaffold-dependent) cells. Herein, as the adherent (scaffold-dependent) cells, there are animal cells such as stem cells including mesenchymal stem cell (MSC) or the like, fibroblast cells, and the like. As mentioned above, attention has been paid to stem cells in development of regenerative medicine or drug discovery. Therefore, the bioreactor of the present invention can be suitably used in culturing of stem cells. That is, the present invention provides a method for culturing a cell using the bioreactor of the present invention. Herein, the method for culturing a cell is not particularly limited, and a general culturing method can be applied similarly or appropriately modified and then applied.

EXAMPLES

The effects of the present invention will be described using the following examples and comparative examples. However, the technical scope of the present invention is not limited to only the following examples. Incidentally, in the following examples, operations were carried out at room temperature (25° C.) unless otherwise specified. In addition, unless otherwise specified, "%" and "part" mean "% by weight" and "parts by weight," respectively.

Production of Polymer

Production Example 1: Synthesis of Polymer 1

To a 20-ml glass pressure-proof test tube, 1.95 g (0.0125 mol) of tetrahydrofurfuryl acrylate, 0.2 g (0.0014 mol) of carboxyethyl acrylate, and 3 g of ethanol were added, and then nitrogen gas was bubbled for 10 seconds. Then, 0.004 g (0.013 mmol) of 2,2'-azobis(4-methoxy-2,4-dimethylvaleronitrile) as a polymerization initiator was added, and heating was performed by a heat block set at 45° C. for 6 hours. The polymerization liquid was added to 50 ml of hexane, and the precipitated polymer component was recovered and dried under reduced pressure, thereby obtaining a copolymer of tetrahydrofurfuryl acrylate (THFA) and carboxyethyl acrylate (CEA) (THFA:CEA=90:10 (structural unit molar ratio), hereinafter, referred to as the polymer 1). The weight average molecular weight of the polymer 1 was 49,500.

Production Example 2: Synthesis of Polymer 2

To a 20-ml glass pressure-proof test tube, 1.65 g (0.0106 mol) of tetrahydrofurfuryl acrylate, 0.38 g (0.0026 mol) of carboxyethyl acrylate, and 3 g of ethanol were added, and then nitrogen gas was bubbled for 10 seconds. Then, 0.004 g (0.013 mmol) of 2,2'-azobis(4-methoxy-2,4-dimethylvaleronitrile) as a polymerization initiator was added, and heating was performed by a heat block set at 45° C. for 6 hours. The polymerization liquid was added to 50 ml of hexane, and the precipitated polymer component was recovered and dried under reduced pressure, thereby obtaining a copolymer of tetrahydrofurfuryl acrylate (THFA) and carboxyethyl acrylate (CEA) (THFA:CEA=80:20 (structural unit molar ratio), hereinafter, referred to as the polymer 2). The weight average molecular weight of the polymer 2 was 46,000.

Production Example 3: Synthesis of Polymer 3

To a 20-ml glass pressure-proof test tube, 1.24 g (0.0079 mol) of tetrahydrofurfuryl acrylate, 0.76 g (0.0053 mol) of carboxyethyl methacrylate, and 3 g of methanol were added, and then nitrogen gas was bubbled for 10 seconds. Then, 0.004 g (0.013 mmol) of 2,2'-azobis(4-methoxy-2,4-dimethylvaleronitrile) as a polymerization initiator was added, and heating was performed by a heat block set at 45° C. for 6 hours. The polymerization liquid was added to 50 ml of hexane, and the precipitated polymer component was recovered and dried under reduced pressure, thereby obtaining a copolymer of tetrahydrofurfuryl acrylate (THFA) and carboxyethyl acrylate (CEA) (THFA:CEA=60:40 (structural unit molar ratio), hereinafter, referred to as the polymer 3). The weight average molecular weight of the polymer 3 was 15,000.

Production Example 4: Synthesis of Polymer 4

To a 20-ml glass pressure-proof test tube, 2.00 g (0.0128 mol) of tetrahydrofurfuryl acrylate and 3 g of methanol were added, and then nitrogen gas was bubbled for 10 seconds. Then, 0.004 g (0.013 mmol) of 2,2'-azobis(4-methoxy-2,4-dimethylvaleronitrile) as a polymerization initiator was added, and heating was performed by a heat block set at 45° C. for 6 hours. The polymerization liquid was added to 50 ml of hexane, and the precipitated polymer component was recovered and dried under reduced pressure, thereby obtaining a homopolymer of tetrahydrofurfuryl acrylate (THFA) (THFA:CEA=100:0 (structural unit molar ratio), hereinafter, referred to as the polymer 4). The weight average molecular weight of the polymer 4 was 55,000.

Production Example 5: Synthesis of Polymer 5

To a 20-ml glass pressure-proof test tube, 0.81 g (0.0052 mol) of tetrahydrofurfuryl acrylate, 1.11 g (0.0077 mol) of carboxyethyl methacrylate, and 3 g of methanol were added, and then nitrogen gas was bubbled for 10 seconds. Then, 0.004 g (0.013 mmol) of 2,2'-azobis(4-methoxy-2,4-dimethylvaleronitrile) as a polymerization initiator was added, and heating was performed by a heat block set at 45° C. for 6 hours. The polymerization liquid was added to 50 ml of hexane, and the precipitated polymer component was recovered and dried under reduced pressure, thereby obtaining a copolymer of tetrahydrofurfuryl acrylate (THFA) and carboxyethyl acrylate (CEA) (THFA:CEA=40:60 (structural unit molar ratio), hereinafter, referred to as the polymer 5). The weight average molecular weight of the polymer 5 was 14,500.

Coating to Substrate

Example 1

The polymer 1 obtained in Production Example 1 described above was dissolved in a mixed solvent of water/ethanol (volume ratio 1/9) to prepare a polymer solution having a polymer concentration of 1% by weight. A commercially available hydrophilic polyether sulfone membrane (hydrophilic PES membrane, pore size: 0.1 μm, manufactured by Membrane Solutions Limited, contact angle of the surface to water: 20°) was immersed in the polymer solution and left to stand still. The hydrophilic PES membrane was taken out and dried at room temperature for 50 hours to obtain a cell culture film 1 having the coating layer.

Examples 2 and 3 and Comparative Examples 1 and 2

A coating layer was formed on the surface of the hydrophilic PES membrane in the similar manner to Example 1, except that, in Example 1, each of the polymers 2 to 5 was used instead of the polymer 1, thereby obtaining cell culture films 2 to 5.

Comparative Example 3

A commercially available hydrophilic polyether sulfone membrane (hydrophilic PES membrane, pore size: 0.1 μm, manufactured by Membrane Solutions Limited, contact angle of the surface to water: 20°) was used as a cell culture film 6.

Results obtained by measuring the contact angle of the surface of the coating layer to water in each cell culture film by the above-described method are presented in the following Table 1.

<Cell Adhesion Activity Assay>

As cells, human adipose tissue-derived mesenchymal stem cells (Lonza, Walkersville, Maryland, U.S.A.) were used. Cells were prepared from a donor who was 22-year-old and Cells expressed CD13, CD29, CD44, CD73, CD90, CD105, SD166≥90%, CD14, CD31, CD45≥5% were used.

The cells were seeded on the 96-well tissue culture polystyrene dishes on which the cell culture films 1 to 6 are disposed, and then cultured for one day in Mesenchymal Stem Cell Growth Medium 2 (PromoCell GmbH, Bedford, Massachusetts, U.S.A.) under humidified condition at 37° C. in the presence of 5% $CO_2$. After the completion of culture, the culture medium was exchanged with Mesenchymal Stem Cell Growth Medium 2 containing 10% WST-1 (Premix WST-1 Cell Proliferation Assay System, Takara Bio Inc., Shiga, Japan) and then cultured for 4 hours under humidified condition at 37° C. in the presence of 5% $CO_2$, and then the absorbance (450 nm, comparison 600 nm) of culture supernatant was measured by a microplate reader and regarded as cell adhesion activity.

Results of cell adhesion activity of each cell culture film are presented in the following Table 1.

TABLE 1

| Cell culture film | Coating | Structural unit molar ratio | | Contact angle (°) | Cell adhesion activity |
|---|---|---|---|---|---|
| | | THEA | CEA | | |
| Example 1 | 1 | Polymer 1 | 90 | 10 | 61 | 0.208 |
| Example 2 | 2 | Polymer 2 | 80 | 20 | 63 | 0.182 |
| Example 3 | 3 | Polymer 3 | 60 | 40 | 68 | 0.160 |
| Comparative Example 1 | 4 | Polymer 4 | 100 | 0 | 60 | 0.135 |
| Comparative Example 2 | 5 | Polymer 5 | 40 | 60 | 62 | 0.110 |
| Comparative Example 3 | 6 | None | — | — | — | 0.080 |

As presented in the above Table 1, the cell culture films 1 to 3 produced using the copolymer having the THFA-derived structural unit and the CEA-derived structural unit in the content range of the present invention exhibited excellent cell adhesion activity as compared to the cell culture film 4 produced using PTHFA. On the other hand, the cell culture film 5 produced using the copolymer which includes the THFA-derived structural unit and the CEA-derived structural unit but does not satisfy the content range of the present invention had poor cell adhesion activity. From the above results, it was found that when the surface treatment is performed using the copolymer according to the present invention, as compared to the case of performing the surface treatment using PTHFA, excellent cell adhesion can be provided to the hydrophilic PES membrane.

The invention claimed is:

1. A cell culture substrate comprising a coating layer on at least one side of a polymer substrate, wherein the coating layer includes a copolymer comprising more than 40% by mole and less than 100% by mole of a structural unit (1) derived from furfuryl (meth)acrylate represented by following Formula (1) and more than 0% by mole and less than 60% by mole of a structural unit (2) comprising an ethylenically unsaturated monomer having a carboxylic group and a (meth)acryloyl group, wherein the total of the structural unit (1) and the structural unit (2) is 100% by mole of the copolymer:

[Chem. 1]

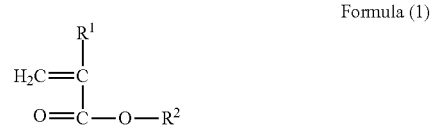

Formula (1)

wherein, $R^1$ represents a hydrogen atom or a methyl group, and $R^2$ represents a group represented by the following Formula (1-1) or the following Formula (1-2):

[Chem. 2]

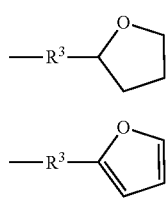

Formula (1-1)

Formula (1-2)

wherein, $R^3$ represents an alkylene group having 1 to 3 carbon atoms, wherein the ethylenically unsaturated monomer is carboxyalkyl (meth)acrylate represented by following Formula (2):

[Chem. 3]

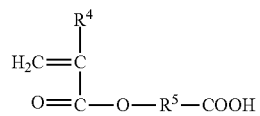

Formula (2)

wherein, $R^4$ represents a hydrogen atom or a methyl group and $R^5$ represents an alkylene group having 2 or 3 carbon atoms.

2. The cell culture substrate according to claim 1, wherein the copolymer is a copolymer having 60 to 95% by mole of the structural unit (1) and 5 to 40% by mole of the structural unit (2), wherein the total of the structural unit (1) and the structural unit (2) is 100% by mole of the copolymer.

3. The cell culture substrate according to claim 1, wherein the copolymer is composed of the structural unit (1) and the structural unit (2).

4. The cell culture substrate according to claim 1, wherein the polymer substrate is a hydrophilic polymer substrate.

5. The cell culture substrate according to claim 1, wherein the polymer substrate contains at least one selected from the group consisting of polyamide, polyethersulfone, polyarylethersulfone, and polyvinylpyrrolidone.

6. A bioreactor comprising the cell culture substrate according to claim 5.

7. A method for culturing a cell using the bioreactor according to claim 6, comprising:

seeding the cell on the cell culture substrate in the bioreactor.

* * * * *